United States Patent
Li

(10) Patent No.: US 8,004,692 B2
(45) Date of Patent: Aug. 23, 2011

(54) OPTICAL INTERFEROMETER AND METHOD

(76) Inventor: Chian Chiu Li, San Jose, CA (US)

( * ) Notice: Subject to any disclaimer, the term of this patent is extended or adjusted under 35 U.S.C. 154(b) by 150 days.

(21) Appl. No.: 11/768,265

(22) Filed: Jun. 26, 2007

(65) Prior Publication Data

US 2008/0024763 A1    Jan. 31, 2008

Related U.S. Application Data

(60) Provisional application No. 60/806,286, filed on Jun. 30, 2006.

(51) Int. Cl.
*G01B 9/02* (2006.01)
(52) U.S. Cl. ........................................ 356/521
(58) Field of Classification Search .......... 356/488, 356/494, 499, 521, 73, 454; 250/237 G, 250/559.19–559.37
See application file for complete search history.

(56) References Cited

U.S. PATENT DOCUMENTS

| | | | | |
|---|---|---|---|---|
| 4,222,667 A * | 9/1980 | Layne | | 356/454 |
| 5,841,583 A | 11/1998 | Bhagavatula | | |
| 6,819,469 B1 * | 11/2004 | Koba | | 359/290 |
| 7,492,948 B2 * | 2/2009 | Gluckstad | | 382/211 |
| 7,768,654 B2 * | 8/2010 | Cui et al. | | 356/521 |
| 2002/0021448 A1 * | 2/2002 | Ishizuka et al. | | 356/488 |
| 2002/0163648 A1 * | 11/2002 | Degertekin et al. | | 356/499 |
| 2003/0038949 A1 * | 2/2003 | Degertekin et al. | | 356/498 |
| 2004/0109168 A1 * | 6/2004 | Fukui | | 356/521 |
| 2005/0152030 A1 * | 7/2005 | Shribak | | 359/386 |
| 2006/0227440 A1 * | 10/2006 | Gluckstad | | 359/885 |
| 2007/0177157 A1 * | 8/2007 | McMurtry et al. | | 356/521 |
| 2008/0158550 A1 * | 7/2008 | Arieli et al. | | 356/73 |

* cited by examiner

*Primary Examiner* — Tarifur Chowdhury
*Assistant Examiner* — Jonathan M Hansen

(57) ABSTRACT

Disclosed are compact optical interferometer array, miniature optical interferometer array, and miniature optical interferometer. The interferometer arrays contain a spatial phase modulator array and a detector array. They are used for conducting multiple measurements. The miniature interferometer has only one component—a spatial phase modulator. Without passing through any focus lens, beam portions coming out of the modulator spread and merge together by themselves. Size of the miniature interferometer can reach subwavelength or even nanoscale. The interferometer array and miniature interferometer find applications in miniature spectrometer, color filter, display, adjustable subwavelength grating, etc.

21 Claims, 7 Drawing Sheets

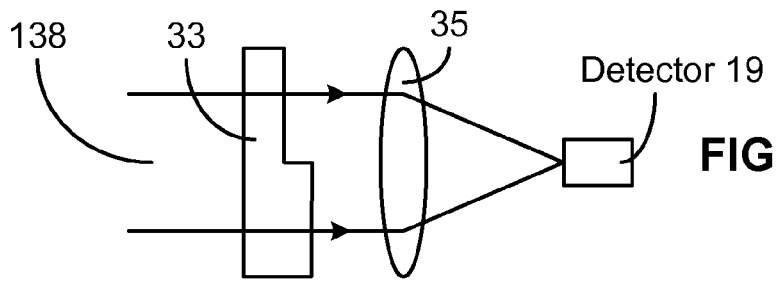
FIG. 1-A (Prior Art)
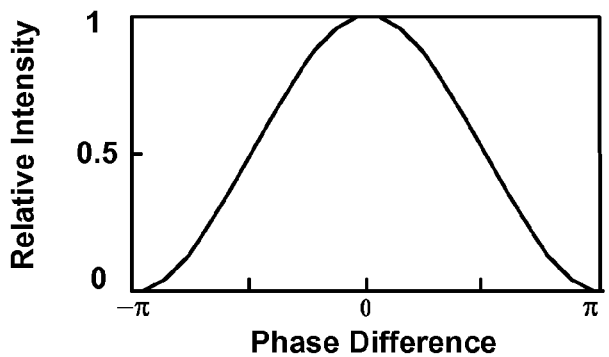
FIG. 1-B (Prior Art)
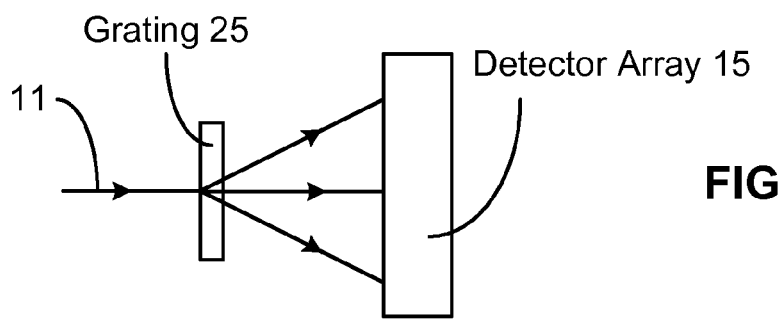
FIG. 1-C (Prior Art)
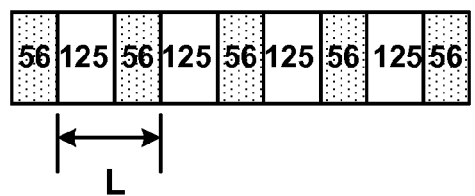
FIG. 1-D (Prior Art)

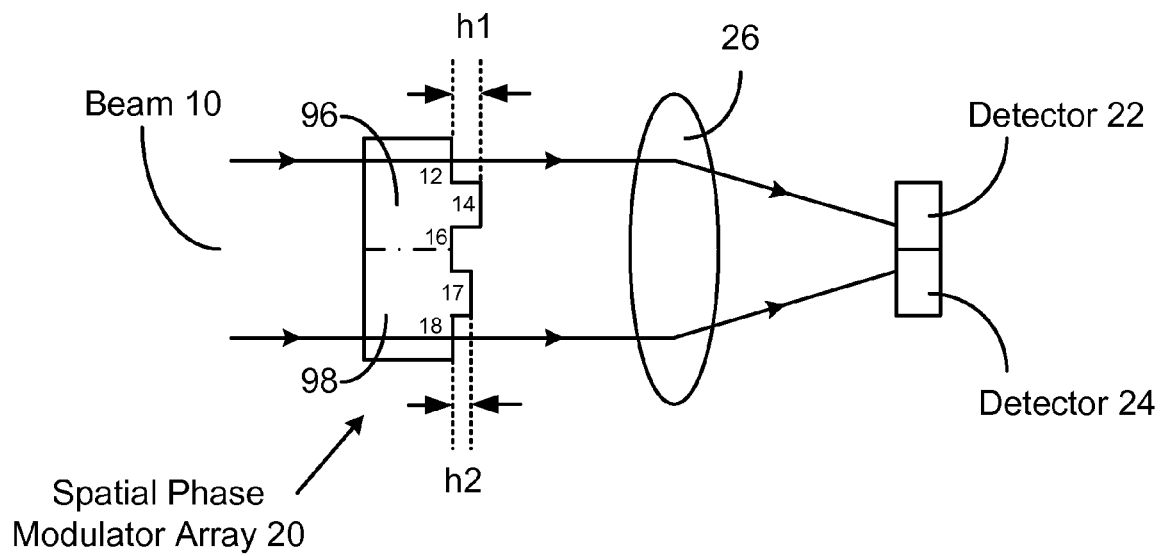
FIG. 2-A
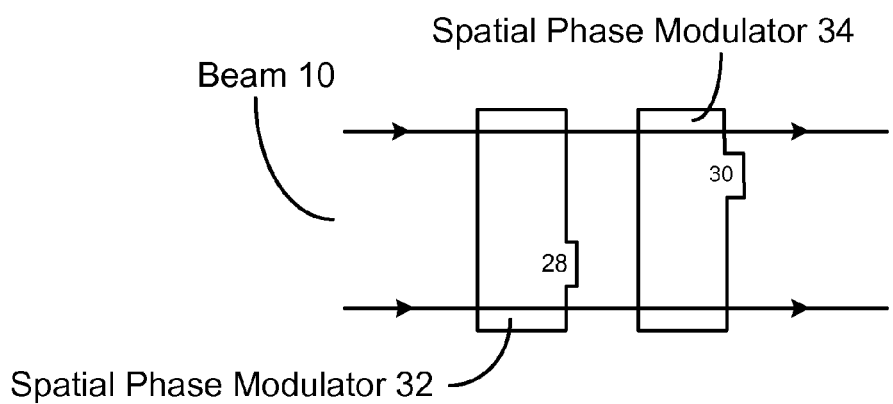
FIG. 2-B

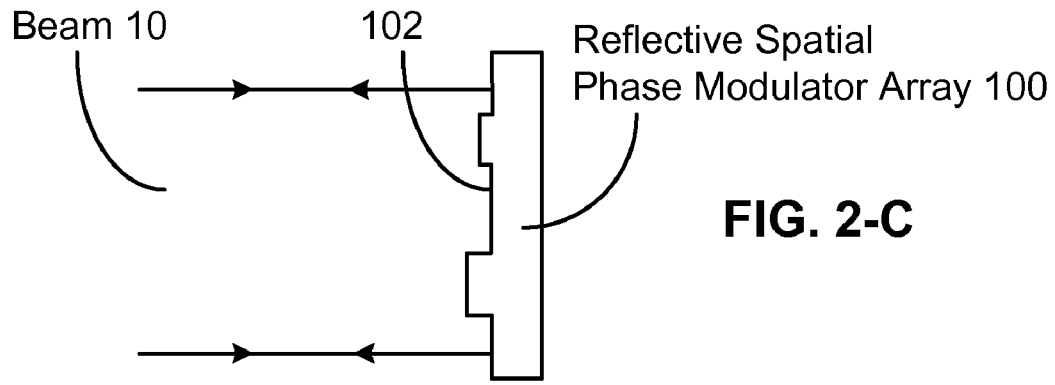
FIG. 2-C
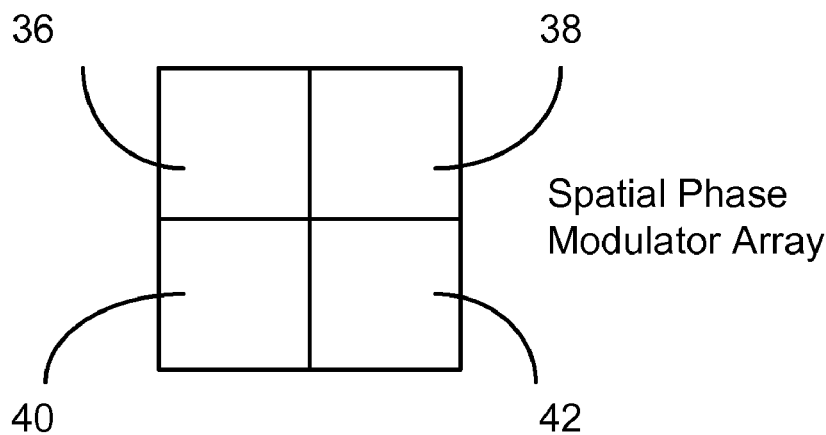
FIG. 3-A
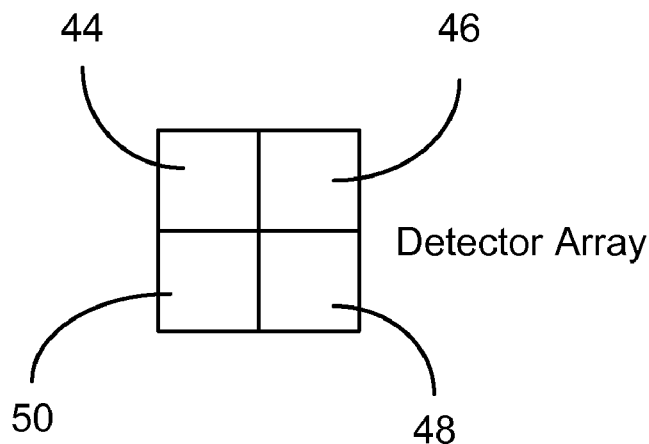
FIG. 3-B

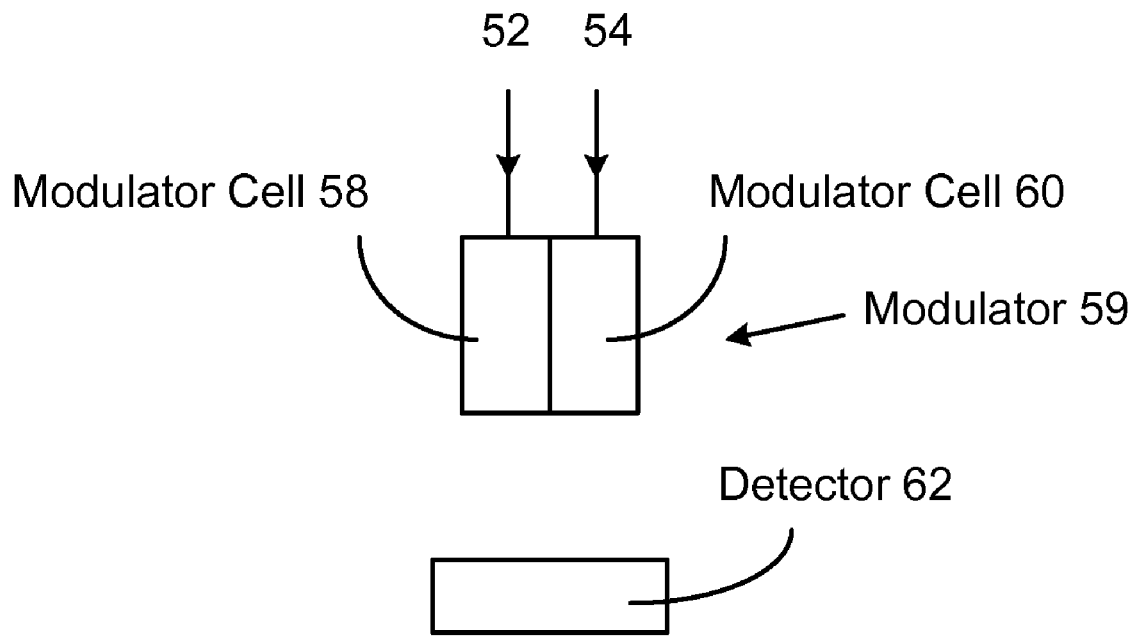
FIG. 4
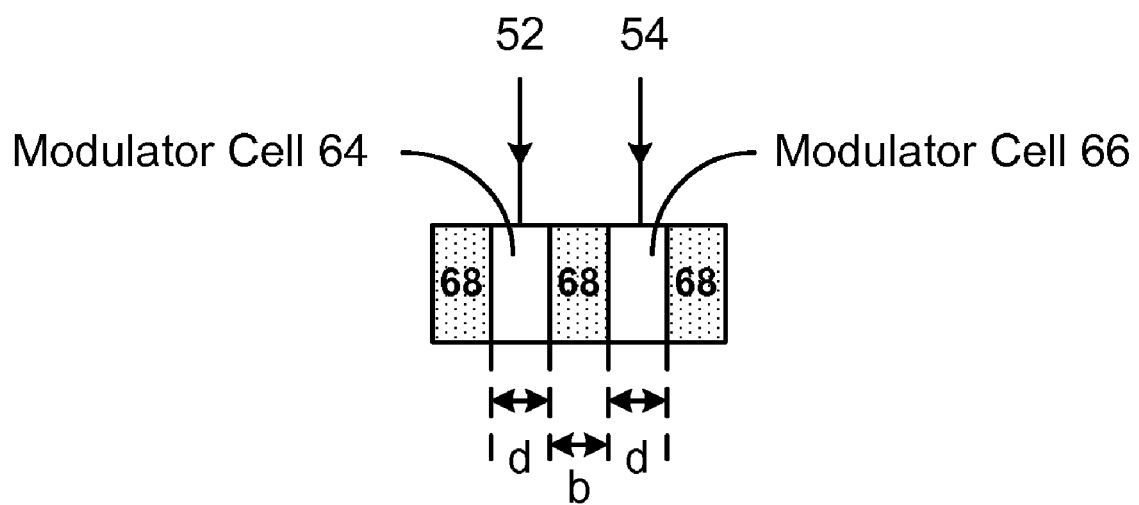
FIG. 5-A

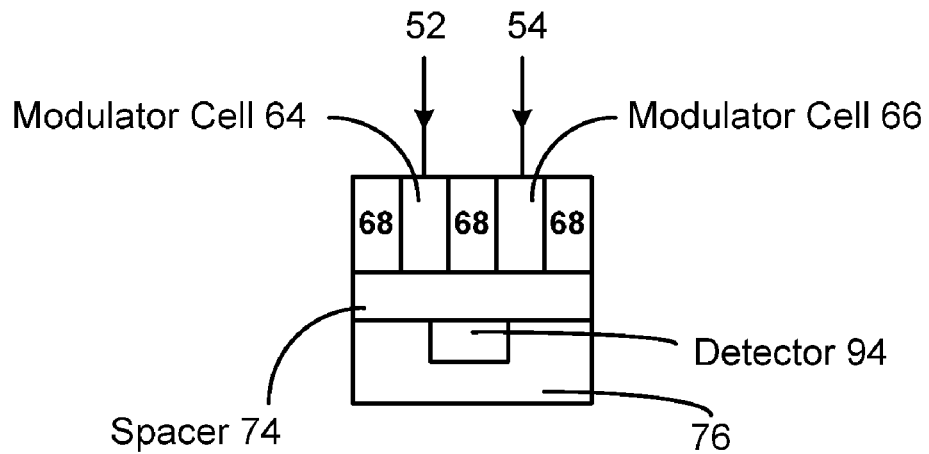
FIG. 5-B
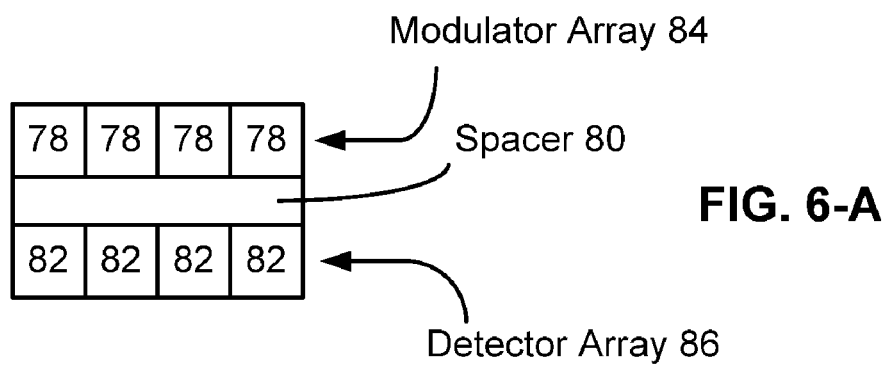
FIG. 6-A
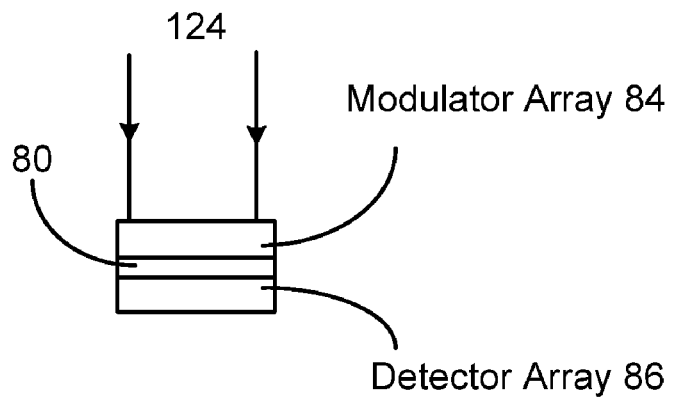
FIG. 6-B

OPTICAL INTERFEROMETER AND METHOD

CROSS REFERENCE TO RELATED APPLICATION

This application is entitled to the benefit of Provisional Patent Application Ser. No. 60/806,286, filed Jun. 30, 2006.

FEDERALLY SPONSORED RESEARCH

Not applicable

SEQUENCE LISTING OR PROGRAM

Not applicable

BACKGROUND

1. Field of Invention

This invention relates to optical interferometer, and particularly to optical interferometer array and miniature optical interferometer.

2. Description of Prior Art

Optical interferometer is an indispensable measurement tool in many fields. It is desirable for an interferometer to make different measurements. It is also desirable to have a small-size interferometer, which is useful for integration with other systems.

Usually, optical interference is created by splitting a beam into two parts either through amplitude division or wavefront division and then recombining the two parts. Amplitude-division may be realized by a beamsplitter and wavefront-division by a spatial phase object. An interferometer using amplitude division tends to have a larger footprint than one using wavefront division, since beams produced by amplitude division are transmitted along optical paths which are separate and head for different directions in most cases, while beams by wavefront division can have side-by-side optical paths, occupying less space.

A traditional interferometer, by amplitude division or wavefront division, is a fixed system and only good for measurement of one type. For different measurements, a tunable interferometer may be used. But a tunable interferometer is often complex and bulky. The other method involves combining a group of discrete interferometers. The interferometers each receive part of a beam respectively. This setup, however, is hardly compact.

Accordingly, there exists a need for an interferometer array, which conducts different measurements and has a compact structure.

One application of interferometer array is of spectrometer. A spectrometer is an optical instrument which measures spectral characteristics of a beam, which in turn reveals physical, chemical, or biochemical information of a sample under test. A compact spectrometer mainly contains two components: a diffraction grating and a detector array. The diffraction grating splits the beam into multiple sub-beams, where each sub-beam corresponds to a specific wavelength. The detector array is arranged such that one detector measures intensity of one sub-beam, or one wavelength. But the detector array has to be placed at a distance far enough from the grating; otherwise, neighboring sub-beams may not separate adequately, which affects resolving resolution. Therefore, current spectrometer has a limit to reduce its dimension.

In order to construct a compact interferometer array, size of individual interferometer should be small. Besides, a small interferometer as a sensor itself is convenient to integrate with a system or other sensors. For such a purpose, as discussed in the above, interferometer using wavefront division is preferred. Currently, two components are needed to build an interferometer by wavefront division: a spatial phase object for creating beam portions having different phase retardation and a focus lens for combining the beam portions to generate interference. In addition, a focus lens has a focal length, which means beam portions are combined at a distance from the lens, or focusing process takes certain space. So the present interferometer dimension is limited by two components and the beam-focusing process.

Therefore, there exists a need for a small-size interferometer which breaks the current limitation on dimension. An interferometer with a small dimension, such as subwavelength-sized or even nano-sized, may lead to other applications besides a compact or miniature interferometer array.

OBJECTS AND ADVANTAGES

Accordingly, several main objects and advantages of the present invention are:

a). to provide an improved optical interferometer which uses wavefront division to split a beam;

b). to provide such an interferometer which contains a spatial phase modulator array and detector array and takes different measurements;

c). to provide such an interferometer which has less component count than the current ones;

d). to provide such an interferometer which has a smaller dimension than the current ones; and e). to provide such an interferometer which can be used for miniature spectrometer, filter, subwavelength grating, etc.

Further objects and advantages will become apparent from a consideration of the drawings and ensuing description.

SUMMARY

In accordance with the present invention, optical interferometers by wavefront division are employed to make a compact interferometer array, a miniature interferometer array, or a miniature interferometer. The interferometer array comprises a spatial phase modulator array and detector array. The miniature interferometer is made possible by using miniature spatial phase modulator. Focus lens is no longer needed to combine beam portions because the beam portions spread and merge together by themselves. The resulting interferometer can be as small as subwavelength or even nano-sized. Applications of the interferometer array and miniature interferometer include miniature spectrometer, filter, color filter, display, and adjustable subwavelength grating.

Abbreviations
  AR anti-reflection
  MEMS micro-electro-mechanical systems
  VOA variable optical attenuator

DRAWING FIGURES

FIGS. 1-A to 1-D illustrate schematically a prior-art optical interferometer, interference curve, spectrometer, and subwavelength grating, respectively.

FIG. 2-A is a schematic cross-sectional view illustrating an embodiment of an optical interferometer array according to the invention.

FIGS. 2-B and 2-C are schematic cross-sectional views illustrating embodiments of spatial phase modulator array according to the invention.

FIGS. 3-A and 3-B are schematic diagrams showing embodiments of spatial phase modulator array and detector array respectively according to the invention.

FIG. 4 is a schematic cross-sectional view illustrating an embodiment of an optical interferometer according to the invention.

FIGS. 5-A and 5-B are schematic cross-sectional views showing embodiments of miniature interferometer according to the invention.

FIGS. 6-A and 6-B are schematic cross-sectional views illustrating embodiments of interferometer array according to the invention.

Figure 7:
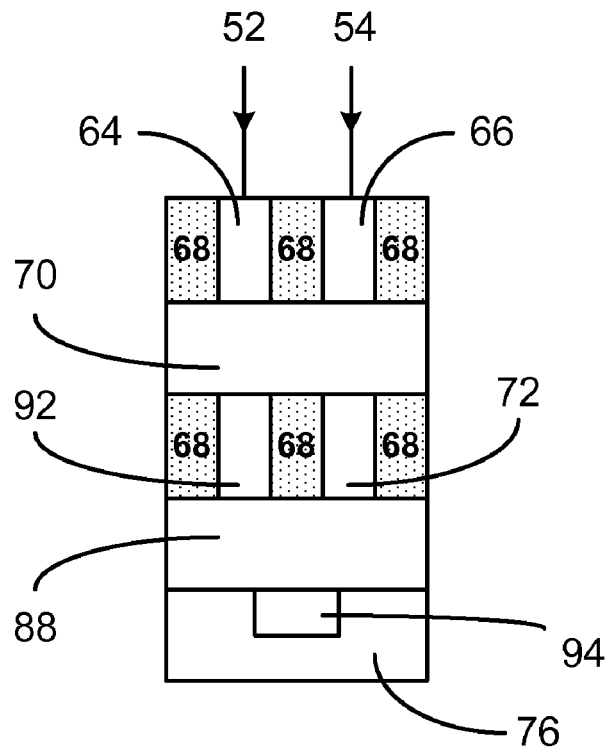
FIGS. 7 and 8 are schematic cross-sectional views showing embodiments of miniature interferometer according to the invention.

| REFERENCE NUMERALS IN DRAWINGS | |
|---|---|
| 10 beam | 11 beam |
| 12 modulator area | 14 modulator area |
| 15 detector array | 16 modulator area |
| 17 modulator area | 18 modulator area |
| 19 detector | 20 modulator array |
| 22 detector | 24 detector |
| 25 grating | 26 lens system |
| 28 modulator area | 30 modulator area |
| 32 spatial phase modulator | 34 spatial phase modulator |
| 36 spatial phase modulator | 38 spatial phase modulator |
| 40 spatial phase modulator | 42 spatial phase modulator |
| 44 detector | 46 detector |
| 48 detector | 50 detector |
| 52 beam portion | 54 beam portion |
| 56 grating element | 58 modulator cell |
| 59 spatial phase modulator | 60 modulator cell |
| 62 detector | 64 modulator cell |
| 66 modulator cell | 68 isolation region |
| 69 grating element | 70 spacer region |
| 72 modulator cell | 74 spacer region |
| 76 substrate | 78 modulator |
| 80 spacer region | 82 detector |
| 84 modulator array | 86 detector array |
| 88 spacer region | 92 modulator cell |
| 94 detector | 96 spatial phase modulator |
| 98 spatial phase modulator | 99 entrance wall |
| 100 modulator array | 102 modulator surface |
| 104 spatial phase modulator | 106 lens system |
| 108 beam | 110 modulator cell |
| 112 modulator cell | 114 modulator cell |
| 116 modulator cell | 117 isolation region |
| 118 beam | 120 modulator cell |
| 122 modulator cell | 124 beam |
| 125 grating element | 126 grating element |
| 127 cell entrance | 128 grating element |
| 130 liquid crystal | 132 grating element |
| 134 grating element | 136 substrate |
| 138 beam | |

DETAILED DESCRIPTION

FIGS. 1-A to 1-D—Prior-Art

FIG. 1-A is a schematic diagram of a prior-art interferometer. A beam 138 is transmitted through a spatial phase modulator 104 and then focused onto a detector 19 by a lens system 106. Modulator 104 divides beam 138 by wavefront division. The beam is split into two beam portions having different phase retardation. Detector 19 measures interference intensity by the beam portions. FIG. 1-B shows a curve of interference intensity versus phase difference. Because phase of a beam is related to its wavelength, the curve indicates the setup may be used as a band pass filter which lets pass of light having a wavelength while blocking light of other wavelengths. Since one interferometer works for selecting one wavelength, a group of interferometers can be used as a spectrometer.

FIG. 1-C shows a prior-art spectrometer using diffraction grating. A diffraction grating contains materials which form a periodic optical structure. In FIG. 1-C, a beam 11 is transmitted to pass through a diffraction grating 25. After interacting with grating 25, beam 11 becomes multiple sub-beams, where each sub-beam is transmitted along a specific angle relative to the grating normal and has a specific wavelength. A detector array 15 is disposed behind grating 25 such that each detector unit receives a sub-beam respectively. By using data of the detector array, spectrum of beam 11 can be obtained, which depicts relation between optical power and wavelength of the beam. Because the sub-beams need a distance to spread apart, detector array 15 has to be placed far enough from grating 25. Therefore, size of the spectrometer can't be reduced beyond a limit.

FIG. 1-D shows schematically a prior art subwavelength grating. The grating contains two repetitive elements 56 and 125, where element 56 may be of metal and element 125 transparent material. Grating elements 125 produce uniform phase retardation for an incoming wavefront. Subwavelength grating features a grating period L which is smaller or much smaller than wavelength of the light. Because of the subwavelength period, only zeroth order diffraction exists.

A subwavelength grating can be designed to be polarization sensitive. When a beam impinges onto it, part of the beam having TM polarization may be transmitted through the grating, while the other part, which has TE polarization, may be reflected by it.

FIGS. 2-A to 2-C and 3-A to 3-B Embodiments of Interferometer Array FIG. 2-A illustrates schematically a cross-sectional view of interferometer array according to the invention. The array comprises a spatial phase modulator array 20, a lens system 26, and detectors 22 and 24. Modulator array 20 is made up of low-loss transmissive materials and contains two spatial phase modulators 96 and 98. The modulators have areas 12, 14, and 16, and 16, 17, and 18, respectively. Modulator array 20 divides an incoming collimated beam 10 into beam portions by wavefront division and phase delays the portions respectively. Because areas 14 and 17 are protruded by height h1 and h2 relative to areas 12, 16, and 18, beam portions going through areas 14 and 17 experience a larger phase delay than those through areas 12, 16, and 18. Next, the beam portions are focused by lens system 26. The modulators and detectors are disposed such that beam portions processed by one modulator go to one detector, while beam portions processed by the other modulator go to the other detector.

Therefore, the interferometer array in FIG. 2-A, containing two interferometers, generates two interference signals simultaneously. Interference intensity of the interferometers is determined by spectrum of the beam and modulators 96 and 98.

A modulator array may also be constructed by modulators disposed in separate places, as shown schematically in FIG. 2-B, where spatial phase modulators 32 and 34 have protruded areas 28 and 30 respectively. Beam 10 is transmitted through modulator 32 first, then modulator 34.

Besides transmissive type, the same result may be realized by a reflective spatial phase modulator array. In FIG. 2-C, beam 10 impinges onto a modulator array 100. The modulator array has a reflective surface 102 which has protruded areas to split a beam into beam portions and phase delay the portions respectively.

It is obvious that an interferometer array may contain more than two units. FIG. 3-A shows a modulator array which is made by spatial phase modulators 36, 38, 40, and 42. FIG. 3-B shows a detector array by detectors 44, 46, 48, and 50. For an interferometer array, the modulator and detector arrays are put together and aligned such that one modulator corresponds to one detector. In other words, the detectors in FIG. 3-B each receive beam portions coming from one modulator in FIG. 3-A, respectively. Because of the modulator and detector array, the resulting interferometer array has a compact structure.

As discussed in the prior art section, one interferometer may function as a spectral filter and multiple interferometers may be used as a spectrometer. Thus an interferometer array, which may have a structure similar to the setup in FIG. 2-A, can work as a compact spectrometer.

FIGS. 4, 5-A, and 5-B Embodiments of Miniature Interferometer

FIG. 4 shows schematically a cross-sectional view of a compact interferometer. A spatial phase modulator 59 has two modulator cells 58 and 60, through which beam portions 52 and 54 pass respectively. After beam portions 52 and 54 come out of the cells, they reach a detector 62. A focus lens might be needed between the modulator and detector to mix the beam portions for creating interference. But if the modulator cells have a dimension small enough in a direction perpendicular to beam propagation, beam portions 52 and 54 would spread after exiting the cells. As a result, the beam portions overlap each other or merge together by themselves to cause interference. Thus, a focus lens is no longer needed.

FIG. 5-A illustrates schematically a cross-sectional view of a miniature interferometer, where beam portions 52 and 54 are transmitted through modulator cells 64 and 66 respectively. Around the modulator cells are isolation regions 68 which blocks light transmission. As shown in FIG. 5-A, modulator cells 64 and 66 have a dimension d and are spaced apart by a distance b along a direction perpendicular to beam propagation. Assume values of d and b are small enough, for example, around or smaller than wavelength of the beam. As a result, beam expansion happens along that direction. Because of beam spreading and a small spacing, beam portions 52 and 54 overlap and merge together within a short distance after coming out of modulator cells 64 and 66, which occurs without help of a focus lens. The overlapped portions cause interference to occur.

A miniature interferometer array may be made using interferometers that have a similar structure to the one in FIG. 5-A. The miniature interferometer array may function as miniature filter array for multiple wavelengths or colors.

The interferometer in FIG. 5-A may also be integrated with a detector, as shown schematically in a cross-sectional view in FIG. 5-B. A detector 94 is fabricated on a substrate 76. A layer 74 works as a spacer region. When beam portions emerge from modulator cells 64 and 66, they spread and mix together in region 74 before impinging onto detector 94. The schemes in FIGS. 5-A and 5-B provide a simple and miniature structure for a modulator or interferometer. Its dimension can be as small as sub-micrometer.

A waveguide or channel may be built in spacer region 74 to convey mixed beam portions to detector 94. The waveguide or channel may reduce power loss. It may also reduce cross-talk when two or more interferometers are placed side-by-side.

FIGS. 6-A & 6-B Embodiment of Miniature Spectrometer

Consider the modulator-detector structure in FIG. 5-B as a cell unit. Multiple such units may be integrated to form a miniature spectrometer. As illustrated schematically in FIGS. 6-A and 6-B, a modulator array 84 contains modulators 78 and a detector array 86 contains detectors 82. Structure of modulator 78 may resemble that in FIG. 5-A. The detectors are built on a common substrate. Each detector contains a photo sensing region facing a corresponding modulator. The modulator and detector arrays are arranged such that a detector receives beam portions coming from only one modulator which is aligned to it. Like region 74, a spacer region 80 is where beam portions from one modulator get merged to cause interference. Since each interferometer functions like a band pass filter for one wavelength, a group of such interferometers may cover certain spectral range.

The modulator and detector array may be made to be one dimensional, or two dimensional similar to that in FIGS. 3-A and 3-B. In an application to measure spectral property of a beam 124, as shown in FIG. 6-B, the beam is transmitted to impinge onto modulator array 84 and then enters spacer region 80. Next interference occurs and interference signals are detected by detector array 86.

Referring back to FIG. 5-B. When portions 52 and 54 are out of phase—meaning the portions experience destructive interference—in region 74, they actually do not pass through the modulator. Instead the portions are reflected back. But in some case, reflected beam portions represents waste of signal power. However, when two interferometers are disposed in a range less than one wavelength of a beam, the beam may reach both interferometers at the same time. If one interferometer rejects the beam due to destructive interference, while the other receives it due to constructive interference, the beam reaches the latter and passes through it. Therefore, such configuration leads to reduction of power loss or more efficient use of signals. The method can be used in applications involving more than two interferometers as well.

Figure 8:
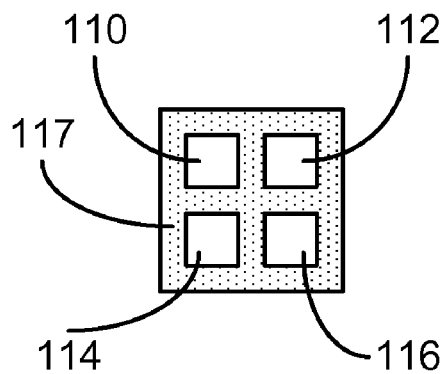

FIGS. 7 & 8 Embodiments of Miniature Interferometer

A plurality of interferometers as in FIG. 5-A may be stacked to create multi-wave interference for an incoming beam. Multi-wave interference has an advantage of narrower pass band over two-wave interference. A narrow pass band means better spectral selection and thus is highly desired in many applications.

With reference to FIG. 7, when beam portions 52 and 54 exit modulator cells 64 and 66, they merge and interfere occurs in a spacer region 70. Then the merged portions enter modulator cells 92 and 72 and two new beam portions are generated by wavefront division. The new beam portions interfere again in a spacer region 88 after leaving cells 72 and 92. Therefore, interference happens twice for the beam portions. There are four interfering waves in region 88 and it is of four-wave interference.

Multiple interferometers having the structure of FIG. 7 may be integrated. Its applications include miniature spectrometer which has better resolution compared to that produced by two-wave interference, or color filter with a narrower pass band.

Another way to create multi-wave interference is illustrated schematically in FIG. 8, which shows a top view of a 4-unit spatial phase modulator. Modulator cells include 110, 112, 114, and 116, which phase delay beam portions (not shown in FIG. 8) respectively. An isolation region 117 separates the cells and blocks light transmission. When four beam portions come out of the modulator cells and mix together, a four-wave interference happens. Assume the four cells generate phase delay zero, alpha, alpha, and two times of alpha on the four beam portions respectively, outcome of the resulting interference resembles that of the two-time interference in FIG. 7.

Figure 9:
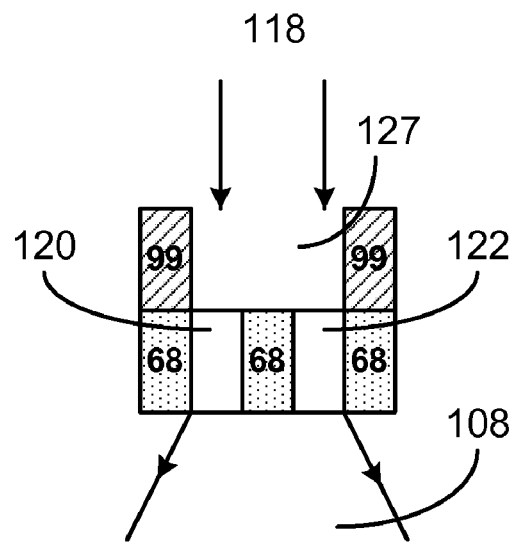
FIG. 9 is a schematic cross-sectional view illustrating an embodiment of a display cell unit according to the invention.

FIG. 9 Embodiment of Display Cell Unit

Scheme of miniature interferometer in FIG. 5-A may also be employed to build a display cell unit. An array of the cell unit may be used to make a display. As illustrated schematically in FIG. 9, a display cell unit is basically a tunable miniature interferometer. When a beam 118 enters a cell entrance 127 and impinges onto the interferometer, modulator cells 120 and 122 create two beam portions, which interfere after coming out to become a viewable beam 108. An entrance wall 99 may be made up of opaque materials, or wall 99 and isolation region 68 may use the same material and be integrated together.

For use in a display, phase difference between the beam portions has to be tunable. Phase tuning may be realized, for example, by using liquid crystal whose refractive index is tuned through changing electrical field applied on it. Phase difference change leads to change of interference intensity between the beam portions, meaning output power or brightness of the display cell is tuned. Color filters may be added to a cell unit to make a color-display cell unit.

Since a band pass filter works like a color filter, the color filter may be replaced by an interferometer structure discussed in the above.

The display cell unit in FIG. 9 may also use a stack structure as in FIG. 7, or multiple-cell structure as in FIG. 8. In a stack scheme, one interferometer may function as a color filter, while the other as a brightness controller.

Figure 10:
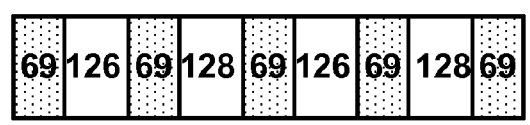
FIGS. 10 and 11 are schematic cross-sectional views showing embodiments of adjustable subwavelength grating according to the invention.
Figure 11:
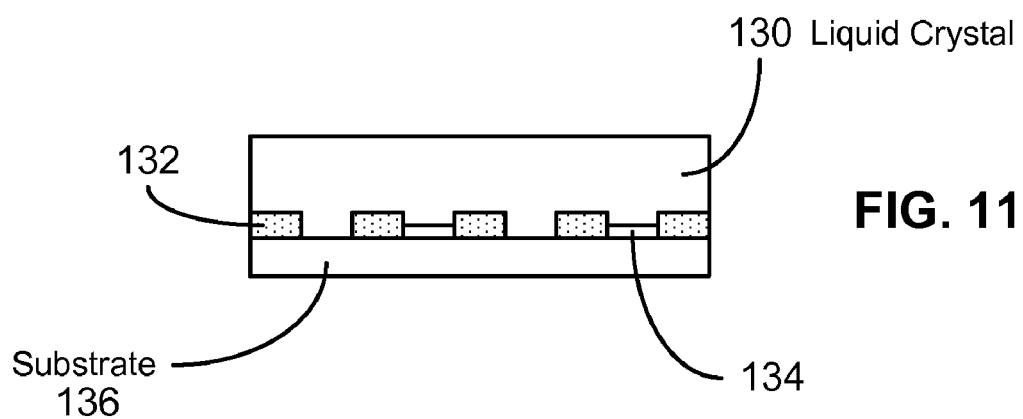

FIGS. 10 & 11 Embodiments of Subwavelength Grating

FIG. 10 shows schematically in a cross-sectional view a novel adjustable subwavelength grating. There are three grating elements: an element 69 which stops light propagation, and alternatively arranged transmissive grating elements 126 and 128. Elements 126 and 128 are designed such that they may generate different phase delay to incoming beam portions. As a consequence, the grating produces two groups of beam portions. One group emerging from one transmissive element may have different phase retardation with respect to the other group. In other words, neighboring beam portions may have different phase and they spread to overlap each other after exiting the grating. When grating elements 126 and 128 produce the same phase retardation, the grating becomes a traditional subwavelength grating, where TE polarization of the beam may be reflected by and TM polarization transmitted through the grating. But when the grating elements produce a phase difference of pai for the two beam portion groups, destructive interference occurs. Consequently, TM polarization, like TE polarization, is reflected by the grating as well.

When element 126 or 128 contains electro-optical materials, such as liquid crystal, phase delay can be adjusted and the TM polarization may be switched between transmission and reflection. Other methods to change phase delay of the beam portions may be employed as well.

FIG. 11 depicts schematically a tunable subwavelength grating using liquid crystal. On a substrate 136, there are opaque grating elements 132 and transmissive grating element 134. Element 132 stops light propagation, while element 134 introduces an initial phase difference between two neighboring beam portions. Partially surrounding the grating elements is liquid crystal. Transparent electrodes (not shown in FIG. 11) are used to control refractive index of the liquid crystal, which in turn changes phase difference of neighboring beam portions. Therefore interference intensity or transmission of TM polarization can be tuned.

CONCLUSION, RAMIFICATIONS, AND SCOPE

Thus it can be seen that I have provided improved interferometer array and interferometer using novel structures and principles.

The interferometer array has the following advantages:
(1) Ability to conduct different measurements.
(2) Compact structure (due to use of modulator and detector array).

The interferometer has the following advantages:
(1) Elimination of focus lens (due to spread beam portions).
(2) Miniature dimension.

Although the description above contains many specificities, these should not be construed as limiting the scope of the invention but as merely providing illustrations of some of the presently preferred embodiments. Numerous modifications, alternations, and variations will be obvious to those skilled in the art.

For example, a transmission-type spatial phase modulator or interferometer may become tunable by using electro-opto materials, such as liquid crystal or lithium niobate. For a reflection-type spatial phase modulator, a deformable structure can be used. Such structure may employ a micro-electro-mechanical systems (MEMS) mirror array, where a mirror is moved up and down to create phase change by a MEMS actuator.

For structures discussed above, any surface where a beam passes through shall have an anti-reflection (AR) coating.

When a miniature interferometer is tunable, it may be used to block or let pass of a variable wavelength band, which results in a tunable color filter, or a variable optical attenuator (VOA).

Lastly, the structure in FIG. 11 may be modified a little and used to create a tunable miniature interferometer by using schemes in FIG. 5-A.

Therefore the scope of the invention should be determined by the appended claims and their legal equivalents, rather than by the examples given.

What is claimed is:
1. An optical apparatus comprising:
a plurality of spatial phase modulators, said modulators each comprising a plurality of side-by-side regions, said regions having a transmissive medium respectively, said modulators being arranged to divide an optical beam into at least a plurality of first beam portions and a plurality of second beam portions by wavefront division, said apparatus being arranged to transmit said first and second beam portions through said regions simultaneously and respectively, said regions being arranged for producing predetermined phase shift on said first and second beam portions respectively;

said apparatus arranged such that said modulators influence said first and second beam portions only once;

isolation means for reducing crosstalk between one of said first and one of said second beam portions, said isolation means comprising a structure for separating one of said first beam portions and one of said second beam portions;

interference means for producing optical interference among said first beam portions and among said second beam portions respectively; and a plurality of detectors for detecting a plurality of signals of said interference respectively.

2. The apparatus according to claim 1 wherein at least one of said first or second beam portions is arranged such that it spreads substantially along a direction perpendicular to its propagation within a substantially short distance.

3. The apparatus according to claim 1 wherein at least two of said first beam portions are disposed such that they are spaced apart by a distance around or smaller than the wavelength of said optical beam.

4. The apparatus according to claim 1 wherein said modulators and said detectors are arranged to be integrated together.

5. An optical interferometric method, comprising:
dividing an optical beam into at least a plurality of first beam portions and a plurality of second beam portions by wavefront division using a plurality of spatial phase modulators;
said method arranged such that said modulators influence said first and second beam portions only once and said modulators each comprise a plurality of side-by-side regions, said regions having a transmissive medium respectively;
transmitting said first and second beam portions through said regions simultaneously for producing predetermined phase shift on said first and second beam portions respectively;
reducing crosstalk between one of said first and one of said second beam portions using a separation structure;
generating optical interference among said first beam portions and among said second beam portions respectively; and
receiving a plurality of signals of said interference respectively.

6. The method according to claim 5 wherein said dividing step is arranged such that at least one of said first or second beam portions spreads substantially along a direction perpendicular to its propagation within a substantially short distance.

7. The method according to claim 5 wherein said dividing step is arranged such that at least two of said first beam portions are spaced apart by a distance around or smaller than the wavelength of said optical beam.

8. The method according to claim 5, further including tuning the phase of one of said first or second beam portions.

9. An optical apparatus comprising:
a plurality of side-by-side first regions for transmitting a plurality of beam portions simultaneously and respectively and producing predetermined phase shift on said beam portions respectively, said first regions having a transmissive medium respectively;
said apparatus arranged such that said first regions influence said beam portions only once;
said apparatus arranged such that said beam portions are disposed side by side along a direction in a second first region after exiting said first regions, the beam width of said beam portions along said direction in said second region is smaller than the wavelength of said beam portions, and the dimension of said second region along said direction is smaller than fifty times of said wavelength, said beam portions arranged to spread and interfere with each other substantially in a third region for generating at least one spreading beam within a distance shorter than 0.1 millimeters, said second region arranged adjacent to said first regions, said third region arranged adjacent to said second region;
and usage means for receiving said spreading beam within 0.5 millimeters from said second first region.

10. The apparatus according to claim 9 wherein said usage means and said first regions are integrated.

11. The apparatus according to claim 9, further including tuning means for tuning the phase of one of said beam portions.

12. An optical interferometric method, comprising:
transmitting a plurality of beam portions through a plurality of side-by-side first regions simultaneously and respectively for producing predetermined phase shift on said beam portions respectively, said first regions having a transmissive medium respectively;
disposing said beam portions side by side along a direction in a second region using optical means, the beam width of said beam portions along said direction in said first second region being arranged smaller than the wavelength of said beam portions, the dimension of said second region along said direction being arranged smaller than fifty times of said wavelength;
said method arranged such that said first regions influence said beam portions only once;
said beam portions being disposed such that they spread, mix, and interfere with each other substantially in a third region for producing at least one spreading beam within a distance shorter than 0.1 millimeters, said second region arranged adjacent to said first regions, said third region arranged adjacent to said second region;
and receiving said spreading beam within 0.5 millimeters from said second region.

13. The method according to claim 12 wherein said receiving step includes detecting said spreading beam.

14. The method according to claim 12, further including tuning the phase of one of said beam portions.

15. An optical apparatus comprising:
a spatial phase modulator, said modulator comprising a plurality of side-by-side first regions, said first regions having a transmissive medium respectively;
optical means for arranging a first beam to pass through said modulator;
said modulator arranged to divide said first beam by wavefront division for generating a plurality of beam portions and to transmit said beam portions through said first regions simultaneously and respectively, said first regions arranged for producing predetermined phase shift on said beam portions respectively, said modulator configured for disposing said beam portions side by side along a direction in a second region;
said apparatus arranged such that said modulator influences said beam portions only once;
said apparatus arranged such that the beam width of said beam portions along said direction in said second region is around or smaller than the wavelength of said first beam and the dimension of said second region is smaller than fifty times of said wavelength along said direction;

said beam portions arranged such that they spread and interfere with each other substantially to generate at least one spreading second beam within a distance shorter than 0.1 millimeters in a third region, said second region arranged adjacent to said first regions, said third region and usage means for receiving said second beam within 5 millimeters from said second region.

16. The apparatus according to claim 15 wherein said modulator includes a spatial phase modulator array.

17. The apparatus according to claim 15, further including conveying means for transmitting said second beam.

18. An optical interferometric method, comprising:

dividing a first beam by wavefront division for generating a plurality of beam portions using a spatial phase modulator, said modulator comprising a plurality of side-by-side first regions, said first regions having a transmissive medium respectively;

transmitting said beam portions through said first regions simultaneously and respectively;

phase shifting said beam portions by predetermined values using said first regions;

said method arranged such that said modulator influences said beam portions only once;

arranging said beam portions side-by-side along a direction in a second region by said modulator;

said beam portions and said second region arranged such that the beam width of said beam portions along said direction in said second region is around or smaller than the wavelength of said first beam and the dimension of said second region along said direction is smaller than fifty times of said wavelength;

said beam portions arranged such that said beam portions spread, mix, and interfere with each other substantially in a third region for producing at least one spreading second beam within a distance shorter than 0.1 millimeters, said second region arranged adjacent to said first regions, said third region arranged adjacent to said second region;

and receiving said second beam within 5 millimeters from said second region.

19. The method according to claim 18, further including phase tuning one of said beam portions.

20. The method according to claim 18, further including conveying said second beam in said third region.

21. An optical interferometric method, comprising:

disposing a structure, said structure comprising a spatial phase modulator and a detector, said modulator comprising a plurality of side-by-side first regions, said first regions having a transmissive medium respectively, said modulator and detector arranged to be integrated, said structure arranged to be attached to a substrate, said detector arranged above said substrate, said first regions arranged above said detector;

transmitting a first beam to said modulator;

dividing said first beam by wavefront division for generating a plurality of beam portions using said modulator;

transmitting said beam portions through said first regions simultaneously and respectively;

phase shifting said beam portions by predetermined values using said first regions;

arranging said beam portions side by side along a direction in a second region by said modulator;

said method arranged such that said modulator influences said beam portions only once;

said beam portions arranged such that the beam width of said beam portions along said direction in said second region is around or smaller than the wavelength of said first beam;

said method arranged such that said beam portions spread, mix, and interfere with each other substantially in a third region for producing at least one second beam within a substantially short distance, said second region arranged adjacent to said first regions, said third region arranged adjacent to said second region;

and detecting said second beam using said detector.

* * * * *